(12) United States Patent
Romes

(10) Patent No.: US 7,226,206 B2
(45) Date of Patent: Jun. 5, 2007

(54) DYNAMIC HEAT FLOW METER FOR MEASURING THERMAL PROPERTIES OF INSULATION OR THE LIKE, AND CORRESPONDING METHOD

(75) Inventor: Gary E. Romes, Cincinnati, OH (US)

(73) Assignee: Guardian Building Products, Inc., Greer, SC (US)

( * ) Notice: Subject to any disclaimer, the term of this patent is extended or adjusted under 35 U.S.C. 154(b) by 42 days.

(21) Appl. No.: 11/127,316

(22) Filed: May 12, 2005

(65) Prior Publication Data

US 2006/0256835 A1    Nov. 16, 2006

(51) Int. Cl.
*G01K 17/00*    (2006.01)

(52) U.S. Cl. .................................. 374/29; 374/135

(58) Field of Classification Search ............... 374/29, 374/30, 39, 44, 135; 73/25.03, 75, 760; 436/149
See application file for complete search history.

(56) References Cited

U.S. PATENT DOCUMENTS

| | | | | |
|---|---|---|---|---|
| 3,123,996 A | * | 3/1964 | Musial ........................ | 374/29 |
| 4,155,244 A | | 5/1979 | Bhattacharyya | |
| 4,534,663 A | * | 8/1985 | Poppendiek et al. .......... | 374/43 |
| 4,553,852 A | * | 11/1985 | Derderian et al. ............. | 374/1 |
| 4,630,938 A | * | 12/1986 | Piorkowska-Palczewska et al. ........................... | 374/44 |
| 5,667,301 A | * | 9/1997 | Jurkowski et al. ............ | 374/43 |
| 5,702,185 A | * | 12/1997 | Heikal ......................... | 374/29 |
| 5,940,784 A | | 8/1999 | El-Husayni | |
| 6,183,128 B1 | * | 2/2001 | Beran et al. .................. | 374/44 |
| 6,331,075 B1 | * | 12/2001 | Amer et al. .................. | 374/44 |
| 6,408,256 B1 | * | 6/2002 | Hittle et al. ................. | 702/130 |
| 6,487,866 B1 | * | 12/2002 | Fesmire et al. .............. | 62/51.1 |
| 6,896,405 B2 | * | 5/2005 | Osone et al. ................. | 374/43 |
| 6,991,366 B2 | * | 1/2006 | Naka et al. .................... | 374/44 |
| 7,077,563 B2 | * | 7/2006 | Xiao et al. .................... | 374/29 |
| 2002/0136261 A1 | * | 9/2002 | Naka et al. .................... | 374/44 |
| 2005/0105584 A1 | * | 5/2005 | Ichikawa et al. ............. | 374/44 |
| 2005/0150887 A1 | * | 7/2005 | Taya et al. .................... | 219/548 |

OTHER PUBLICATIONS

"Dynamic Insulation A Theoretical Analysis of Thermal Insulation Through Which a Gas or Fluid Flows", Anderlind et al., Swedish Council for Building Research, Document D8:1983.

* cited by examiner

*Primary Examiner*—Gail Verbitsky
(74) *Attorney, Agent, or Firm*—Nixon & Vanderhye P.C.

(57) ABSTRACT

A dynamic heat flow meter is provided which introduces a measured air flow into the system adjacent the test sample (e.g., insulation product), for which thermal properties are to be measured. The heat flow meter then measures thermal properties (e.g., thermal conductivity and/or heat capacity) of the test sample taking into account air flow through and/or adjacent the test sample.

16 Claims, 2 Drawing Sheets

DYNAMIC HEAT FLOW METER FOR MEASURING THERMAL PROPERTIES OF INSULATION OR THE LIKE, AND CORRESPONDING METHOD

This application relates to a dynamic heat flow meter for measuring the thermal properties of a material (e.g., insulation such as fiberglass inclusive insulation, or any other suitable material). The dynamic heat flow meter takes air flow into account when measuring thermal properties of a material. A corresponding method is also provided.

BACKGROUND OF THE INVENTION

The instant application relates to a heat flow meter, and method, for testing thermal properties of materials including thermal conductivity and/or heat capacity.

Thermal properties, such as thermal conductivity, are important physical properties of solids. Heat flows through a solid that has a temperature gradient across its volume. The thermal conductivity of a specimen can be measured directly by measuring the heat flux resulting from a know temperature gradient across a known thickness.

A one-dimensional form of the Fourier heat flow relation is sometimes used to calculate thermal conductivity under steady-state conditions: $k = Q (\Delta X/\Delta T)$, where "k" is thermal conductivity, "Q" is a heat flow per a unit surface area (heat flux), and $\Delta T$ is a temperature difference over the thickness $\Delta X$.

Prior Art FIG. 1 illustrates a conventional static heat flow meter for measuring the thermal conductivity of a test sample (e.g., piece of insulation such as fiberglass). The test sample or specimen is located between two flat plates, and the plates are maintained at known, but different, temperatures. As heat flows through the test sample from the hot side to the cold side, a heat flux transducer (not shown) measures the amount of heat transferred. Thermocouple(s) or other temperature measuring device(s) measure the temperatures of each of the two plates (i.e., of the so-called hot and cold plates). These values are then plugged into the above-listed equation, so that the thermal conductivity of the test sample or specimen can be calculated based on the measured values. Such measurements are often done in accordance with standard testing methods such ASTM C 518, which is incorporated herein by reference. It is in such a manner that insulation products such as fiberglass batts are assigned so-called "R-values"—based on their steady state or static measured thermal properties per ASTM C 518 (e.g., R11 fiberglass insulation batt, etc.).

Unfortunately, the standard testing device of FIG. 1 discussed above determines thermal properties of the test sample via steady state or static testing, where there is no air flow (i.e., there is zero air movement introduced into the testing equipment during the testing). Thus, measurements from such devices can be deceiving as will be explained below.

When insulation (e.g., fiberglass insulation batt, fiberglass loose-fill, cellulose loose-fill, combination/laminate of fiberglass and foam insulation, or the like) is provided in a vertical wall cavity of a home (e.g., between two-by-four studs as is known in the art), it has been found that air flow (e.g., due to wind or the like in the environment surrounding or adjacent to the home) through the wall can have an affect on insulation properties. Contributions to total building heating or cooling load include the change in enthalpy of air moving through an insulation (e.g., fiberglass) and the heat flux through the insulation due to the imposed thermal gradient. The two effects are not independent since the air movement affects the temperature distribution in the insulation. One may experience an example of air flow in an exterior wall of a home by feeling a cool draft in the winter when one puts his or her hand adjacent an electrical outlet. Such air flows in or through walls can reduce the thermal performance of insulation, since insulation such as fiberglass is not an air barrier as it does not stop air flow.

Heretofore, there has been no efficient way to measure the effect of air flow on insulation products. In particular, there has been no way to quantify how much air flow reduces the thermal performance of certain insulation products. Unfortunately, the conventional heat flow meter shown in FIG. 1 and discussed above does not take air flow into account when measuring thermal properties of the test sample.

In view of the above, it will be apparent to those skilled in the art that there exists a need in the art for a heat flow meter, and method, for measuring thermal properties of a product (e.g., insulation product) in a manner which takes into account dynamic air flow.

BRIEF SUMMARY OF EXAMPLES OF THE INVENTION

In certain example embodiments of this invention, a heat flow meter is provided which introduces a measured air flow into the system adjacent the test sample (e.g., insulation product) to be measured. The heat flow meter then measures thermal properties (e.g., thermal conductivity and/or heat capacity) of the test sample taking into account air flow through the test sample.

By taking into account intentionally introduced and measured air flow through and/or across the test sample, one can determine how effective the particular sample would be in real-world conditions where wind (and thus air flow in/through home walls) is a frequent occurrence. This permits one to determine which types of insulation may be effective in certain types of environments.

In certain example embodiments of this invention, there is provided a method of measuring thermal properties of insulation, the method comprising: in a housing, providing first and second plates; positioning a test sample of insulation between the first and second plates; providing the first and second plates at different temperatures when the test sample is therebetween; introducing an air flow into the cavity on one side of the test sample, and permitting air from the air flow to exit the cavity from the other side of the test sample; and measuring thermal properties of the test sample using each of the air flow and temperatures of the respective first and second plates.

In other example embodiments of this invention, there is provided a dynamic heat flow meter for measuring thermal properties of insulation, the dynamic heat flow meter comprising: a housing defining at least one cavity therein; first and second plates at least partially provided in the housing, wherein a test sample of insulation is to be provided between the first and second plates; means for providing the first and second plates at known, but different, temperatures when the test sample is therebetween; means for introducing an air flow into the cavity on one side of the test sample, and permitting air from the air flow to exit the cavity from the other side of the test sample; and means for measuring thermal properties of the test sample using each of the air flow and temperatures of the respective first and second plates

DETAILED DESCRIPTION OF THE INVENTION

In certain example embodiments of this invention, the aforesaid problems of static or steady-state heat flow meters are addressed and overcome by providing a heat flow meter which intentionally introduces a measured air flow adjacent the test sample (e.g., insulation product such as fiberglass insulation batt, loose-fill fiberglass insulation, loose-fill cellulose insulation, combination or laminate of fiberglass and foam insulation, etc.) to be measured. The air flow may be through and/or across the test sample. The heat flow meter then measures thermal properties (e.g., thermal conductivity and/or heat capacity) of the test sample taking into account air flow through the test sample.

Since an intentionally introduced and measured air flow, which air flow at least partially proceeds through the test sample, is taken into account, one can determine how effective the particular sample would be in real-world conditions where wind (and thus air flow in/through home walls) is a frequent occurrence. This permits one to determine which types of insulation may be effective in certain types of environments.

Figure 1:
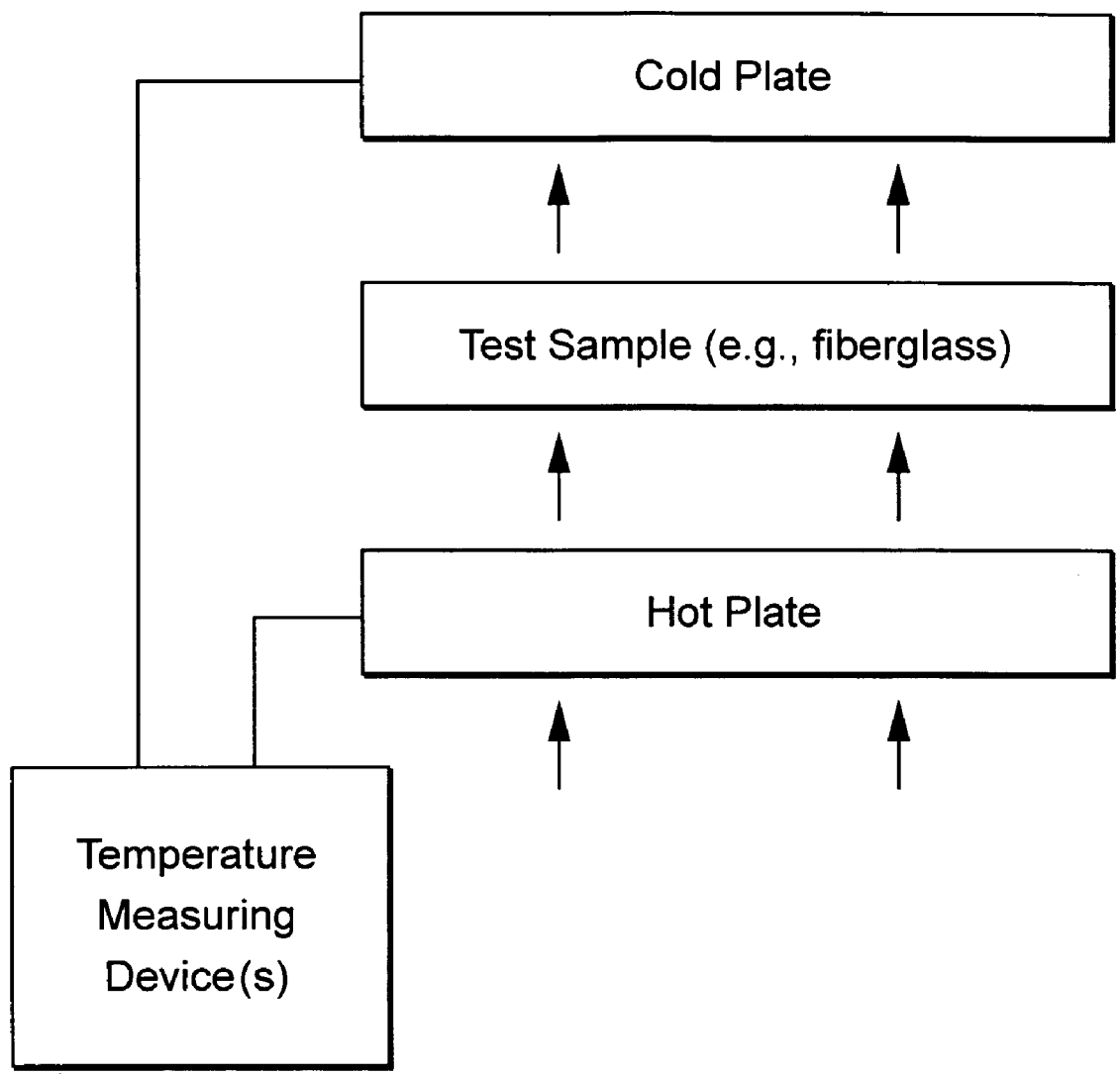
FIG. 1 is a schematic diagram of a conventional steady state or static heat flow meter.
Figure 2:
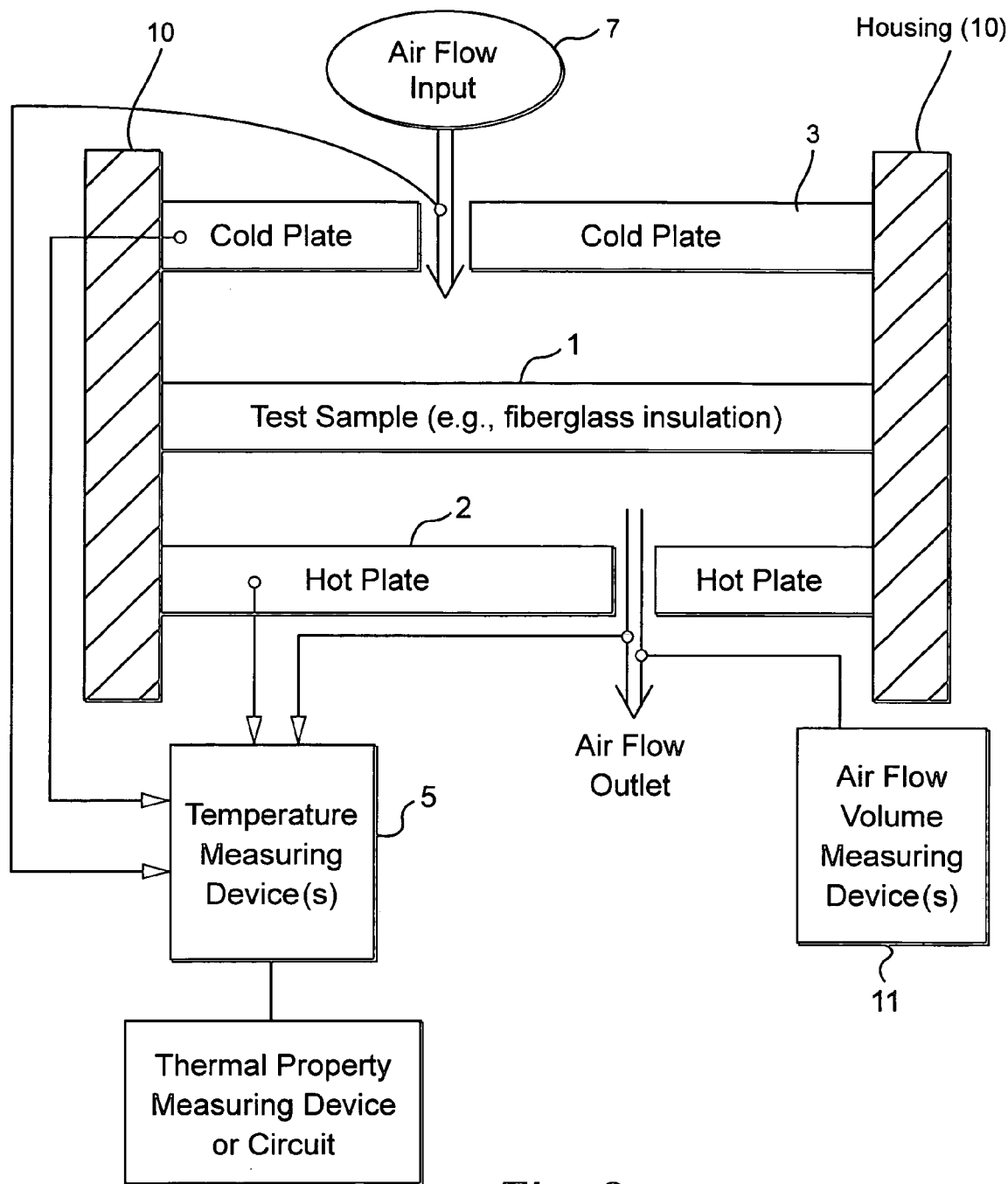
FIG. 2 is a schematic diagram of a dynamic heat flow meter according to an example embodiment of this invention.

FIG. 2 is a schematic diagram illustrating a dynamic heat flow meter according to an example embodiment of this invention. The test sample or specimen (1) to be measured may be an insulation product such as fiberglass insulation batt, loose-fill fiberglass insulation, loose-fill cellulose insulation, combination or laminate of fiberglass and foam insulation, etc. The test sample (1) to be measured is located between two flat plates (2) and (3), and the plates are maintained at known, but different, temperatures. One plate (2) may be considered a hot plate, and the other (3) a cold plate since one is hotter than the other. As heat flows through the test sample (1) from the hot side to the cold side, it is possible for a heat flux transducer (not shown) to measure the amount of heat transferred. Thermocouple(s), thermistor(s), or other temperature measuring device(s) (5) measure the temperatures of each of the two plates (2 and 3).

Still referring to FIG. 2, one or more aperture(s) may be provided in one of the plates (2 or 3) so as to allow a measured air flow from air flow input 7 to be introduced into a cavity of the measuring device and be directed toward and/or adjacent the test sample to be measured. The input air flow is measured (e.g., by volume). For example and without limitation, an example introduced air flow may be about 3 or 4 cubic feet per minute. The input air flow may be introduced either through an aperture(s) in the cold plate (3) as shown in FIG. 2, or alternatively through an aperture(s) in the hot plate (2) (i.e., it may be introduced from either side). At least part of, and preferably all of, the air flow that is introduced from input 7 through the aperture(s) in the plate flows through the test sample 1 and exits the heat flow meter via one or more aperture(s) in the other plate (e.g., see air flow output in FIG. 2).

The housing 10 surrounding the plates and test sample prevents any air flow from leaking out of the device, so that all or substantially all of the introduced air flow is forced to flow through the test sample 1. In certain example instances, a gasket(s) may be provided to improve the seal and make sure than air flow does not escape except through a designed air flow outlet(s). If the air flow volume measuring device 11 at the air flow outlet measures air flow at an amount more than a predetermined amount different than does an air flow volume measuring device (not shown) at the inlet proximate 7, then an alarm may be actuated to indicate that an air flow leak is present in this system.

Temperature measuring device(s) (5) measure the temperature of each of the hot plate, the cold plate, the input air flow, and the output air flow. This information may be used in equation(s) in determining the thermal properties of the test sample.

FIG. 2 illustrates the measured air flow moving through the test sample, in a direction which is parallel to, or anti-parallel to, the heat-flow direction. The air is introduced into the cavity of the meter from an external temperature controlled source. The heat-flow meter with controlled air flow is used to determine total heat-flow rates as a function of air-flow rate, air flow direction, and temperature for commonly used wall cavity insulations for example. It is noted, however, that the direction of air flow in other embodiments may be in different directions.

The heat flow meter thus measures thermal properties (e.g., thermal conductivity and/or heat capacity) of the test sample taking into account air flow through the test sample. For example, if thermal conductivity can be measured as discussed above, with a known and measured air flow through and/or across the test sample 1, the products thermal properties can be determined as a function of air flow.

In certain example embodiments, the intentionally input measured air flow may be introduced into the cavity of the heat flow meter via an aperture(s) in housing 10, instead of an aperture(s) in one of the plates (2 or 3). Thus, in such embodiments, no aperture(s) in plate (3) is needed. It is also possible for the air flow outlet aperture(s) to be defined in housing 10 instead of in one of the plates (2 or 3), so long as the air flow inlet and air flow outlet are provided on opposite sides of the test sample 1. Thus, in certain example embodiments of this invention, there need not be any holes or aperture(s) in plate (2) and/or plate (3).

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

The invention claimed is:

1. A dynamic heat flow meter for measuring thermal properties of insulation, the dynamic heat flow meter comprising:

a housing defining at least one cavity therein;

first and second plates at least partially provided in the housing, wherein a test sample of insulation is to be provided between the first and second plates;

means for providing the first and second plates at known, but different, temperatures when the test sample is therebetween;

means for introducing an air flow into the cavity on one side of the test sample, and permitting air from the air flow to exit the cavity from the other side of the test sample;

means for measuring thermal properties of the test sample using each of the air flow and temperatures of the respective first and second plates; and wherein the first plate has an air flow inlet aperture(s) defined therein, and the second plate has an air flow outlet aperture(s) defined therein.

2. The heat flow meter of claim 1, wherein the test sample includes at least fiberglass insulation.

3. A dynamic heat flow meter for measuring thermal properties of insulation, the dynamic heat flow meter comprising:
   a housing defining at least one cavity therein;
   first and second plates at least partially provided in the housing, wherein a test sample of insulation is to be provided between the first and second plates;
   means for providing the first and second plates at known, but different, temperatures when the test sample is therebetween;
   means for introducing an air flow into the cavity on one side of the test sample, and permitting air from the air flow to exit the cavity from the other side of the test sample;
   means for measuring thermal properties of the test sample using each of the air flow and temperatures of the respective first and second plates; and
   wherein the housing has an air flow inlet aperture(s) defined therein on a first side of the test sample, and the housing further has an air flow outlet aperture(s) defined therein on a second side of the test sample that is opposite the first side.

4. The heat flow meter of claim 3, wherein the test sample includes at least fiberglass insulation.

5. A dynamic heat flow meter for measuring thermal properties of insulation, the dynamic heat flow meter comprising:
   a housing defining at least one cavity therein;
   first and second plates at least partially provided in the housing, wherein a test sample of insulation is to be provided between the first and second plates;
   means for providing the first and second plates at known, but different, temperatures when the test sample is therebetween;
   means for introducing an air flow into the cavity on one side of the test sample, and permitting air from the air flow to exit the cavity from the other side of the test sample;
   means for measuring thermal properties of the test sample using each of the air flow and temperatures of the respective first and second plates; and
   means for measuring the volume of air flow both entering and exiting the cavity of the meter.

6. The heat flow meter of claim 5, wherein the first plate has an air flow inlet aperture(s) defined therein, and the second plate has an air flow outlet aperture(s) defined therein.

7. The heat flow meter of claim 5, wherein the test sample includes at least fiberglass insulation.

8. A dynamic heat flow meter for measuring thermal properties of insulation, the dynamic heat flow meter comprising:
   a housing defining at least one cavity therein;
   first and second plates at least partially provided in the housing, wherein a test sample of insulation is to be provided between the first and second plates;
   means for maintaining the first and second plates at different temperatures when the test sample is therebetween;
   an inlet for introducing a measured and/or known volume of air flow into the cavity on one side of the test sample;
   at least one circuit for measuring thermal properties of the test sample taking into account each of the air flow and temperatures of the respective first and second plates; and
   wherein the housing has an air flow inlet aperture(s) defined therein on a first side of the test sample, and the housing further has an air flow outlet aperture(s) defined therein on a second side of the test sample that is opposite the first side.

9. A method of measuring thermal properties of insulation, the method comprising:
   in a housing, providing first and second plates;
   positioning a test sample of insulation between the first and second plates;
   providing the first and second plates at different temperatures when the test sample is therebetween;
   introducing an air flow into the cavity on one side of the test sample, and permitting air from the air flow to exit the cavity from the other side of the test sample;
   measuring thermal properties of the test sample using each of the air flow and temperatures of the respective first and second plates; and
   wherein the first plate has an air flow inlet aperture(s) defined therein, and the second plate has an air flow outlet aperture(s) defined therein.

10. The method of claim 9, wherein the test sample includes each of fiberglass insulation and foam insulation.

11. The method of claim 9, wherein the test sample includes at least fiberglass insulation.

12. A method of measuring thermal properties of insulation, the method comprising:
   in a housing, providing first and second plates;
   positioning a test sample of insulation between the first and second plates;
   providing the first and second plates at different temperatures when the test sample is therebetween;
   introducing an air flow into the cavity on one side of the test sample, and permitting air from the air flow to exit the cavity from the other side of the test sample;
   measuring thermal properties of the test sample using each of the air flow and temperatures of the respective first and second plates; and
   wherein the housing has an air flow inlet aperture(s) defined therein on a first side of the test sample, and the housing further has an air flow outlet aperture(s) defined therein on a second side of the test sample that is opposite the first side.

13. The method of claim 12, wherein the test sample includes at least fiberglass insulation.

14. A method of measuring thermal properties of insulation, the method comprising:
   in a housing, providing first and second plates;
   positioning a test sample of insulation between the first and second plates;
   providing the first and second plates at different temperatures when the test sample is therebetween;
   introducing an air flow into the cavity on one side of the test sample, and permitting air from the air flow to exit the cavity from the other side of the test sample;
   measuring thermal properties of the test sample using each of the air flow and temperatures of the respective first and second plates; and
   measuring the volume of air flow both entering and exiting the cavity of the meter.

15. The method of claim 14, wherein the first plate has an air flow inlet aperture(s) defined therein, and the second plate has an air flow outlet aperture(s) defined therein.

16. The method of claim 14, wherein the test sample includes at least fiberglass insulation.

* * * * *